(12) United States Patent
Cooper et al.

(10) Patent No.: US 7,863,589 B1
(45) Date of Patent: Jan. 4, 2011

(54) SHOE SANITIZING APPARATUS

(76) Inventors: Sean S. Cooper, 115 Klasey Rd., Morton, WA (US) 98356; Merrell N. Cooper, 115 Klasey Rd., Morton, WA (US) 98356

( * ) Notice: Subject to any disclaimer, the term of this patent is extended or adjusted under 35 U.S.C. 154(b) by 0 days.

(21) Appl. No.: 12/107,887

(22) Filed: Apr. 23, 2008

(51) Int. Cl.
*A61L 2/10* (2006.01)
(52) U.S. Cl. .................................... 250/504 R; 422/24
(58) Field of Classification Search .................. None
See application file for complete search history.

(56) References Cited

U.S. PATENT DOCUMENTS

| | | | |
|---|---|---|---|
| 2,070,858 A | 2/1937 | Jardins et al. | |
| D293,277 S | 12/1987 | Schmid | |
| 4,981,651 A | 1/1991 | Horng | |
| 5,920,075 A | 7/1999 | Whitehead | |
| 5,978,996 A | 11/1999 | Ullman | |
| 6,675,421 B1 | 1/2004 | Hsu | |

FOREIGN PATENT DOCUMENTS

KR 20030097654 * 12/2003
WO WO02007106835 A2 * 9/2007

* cited by examiner

*Primary Examiner*—Elizabeth L Mckane

(57) ABSTRACT

A shoe sanitizing apparatus includes a housing that has a bottom wall, a top wall, a first lateral wall, a second lateral wall, a front wall and a rear wall. The top, bottom, first lateral, second lateral and front walls comprise a transparent material. A light emitter is positioned within the housing. The light emitter emits light having a frequency to kill bacteria. An actuator is operationally coupled to the light emitter and is turned on or off when the actuator is actuated. The housing is positioned within a shoe and the light emitter turned on to kill bacteria in the shoe.

6 Claims, 7 Drawing Sheets

SHOE SANITIZING APPARATUS

BACKGROUND OF THE INVENTION

Field of the Invention

The present invention relates to shoe sanitizing devices and more particularly pertains to a new shoe sanitizing device for killing bacteria by means of a light emitter.

SUMMARY OF THE INVENTION

The present invention meets the needs presented above by generally comprising a housing that has a bottom wall, a top wall, a first lateral wall, a second lateral wall, a front wall and a rear wall. The top, bottom, first lateral, second lateral and front walls comprise a transparent material. A light emitter is positioned within the housing. The light emitter emits light having a frequency to kill bacteria. An actuator is operationally coupled to the light emitter and is turned on or off when the actuator is actuated. The housing is positioned within a shoe and the light emitter turned on to kill bacteria in the shoe.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
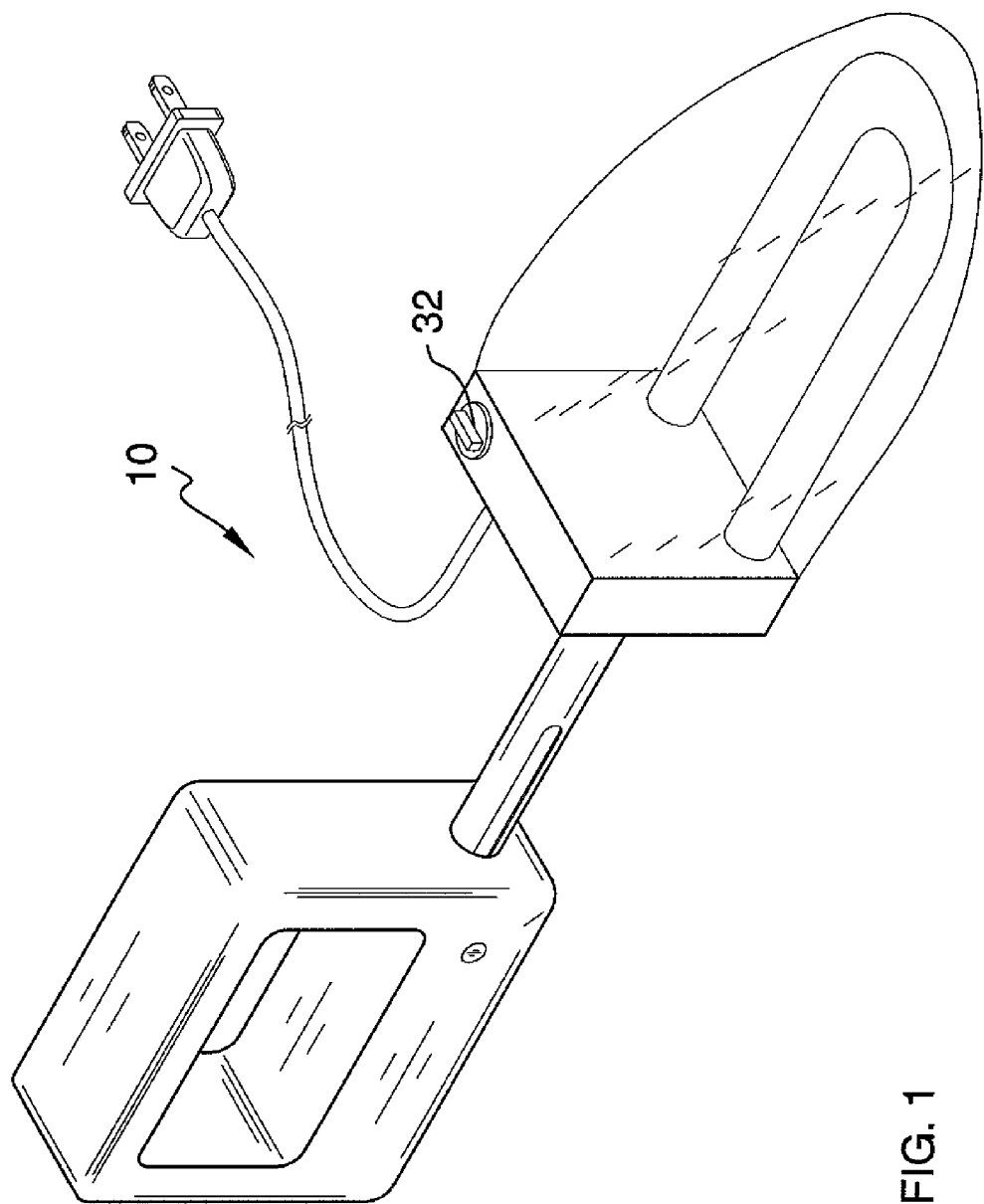
FIG. 1 is a front perspective view of a shoe sanitizing apparatus according to the present invention.
Figure 2:
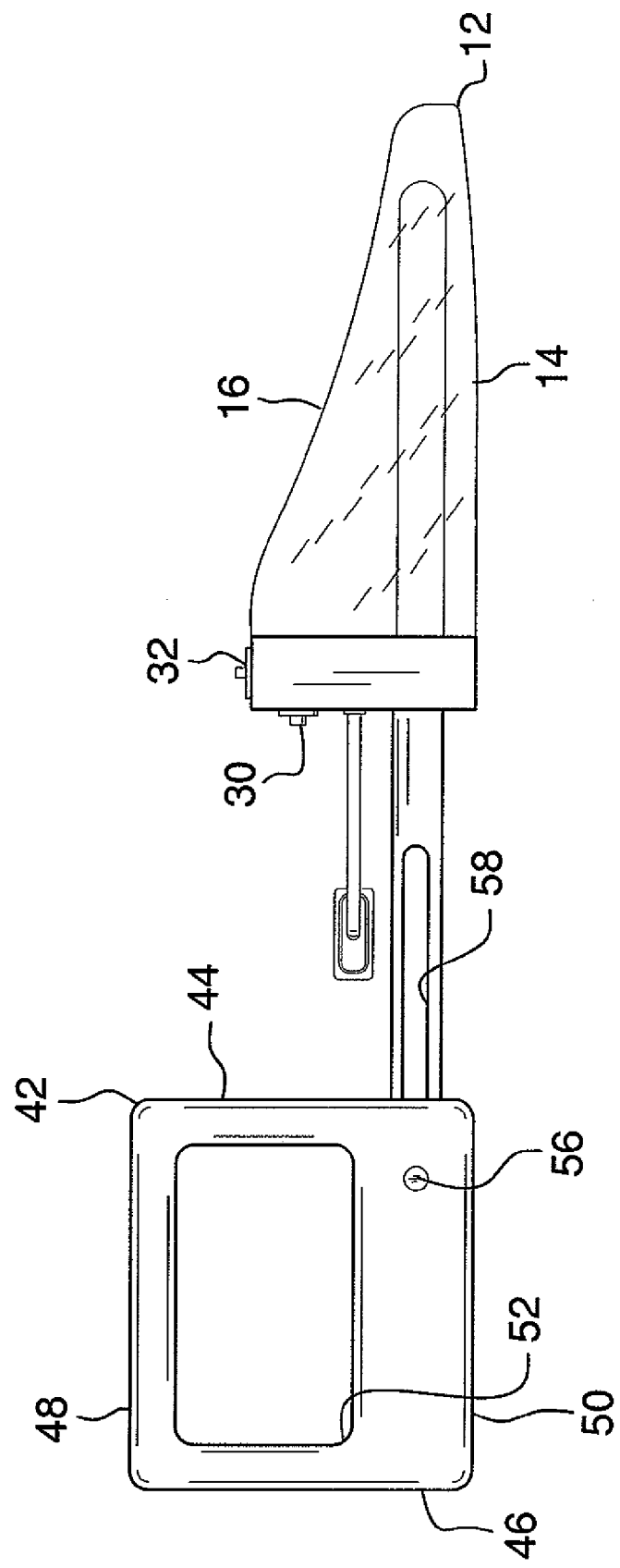
FIG. 2 is a side view of the present invention.
Figure 3:
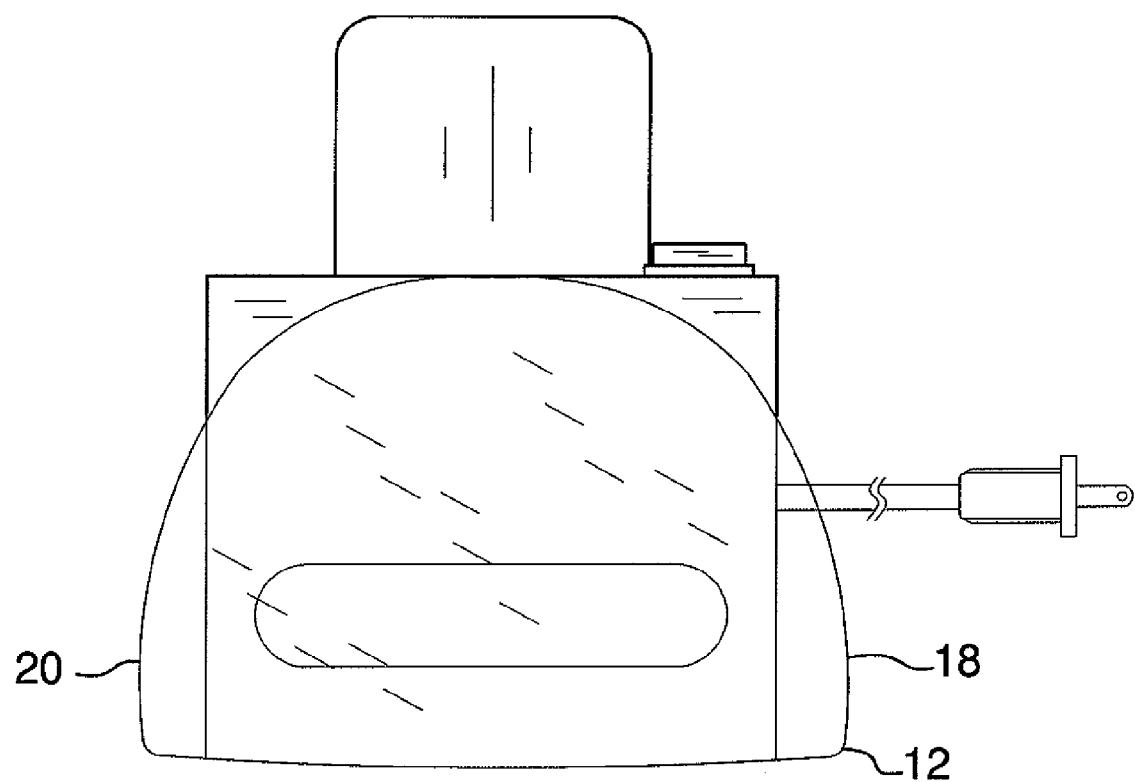
FIG. 3 is a front view of the present invention.
Figure 4:
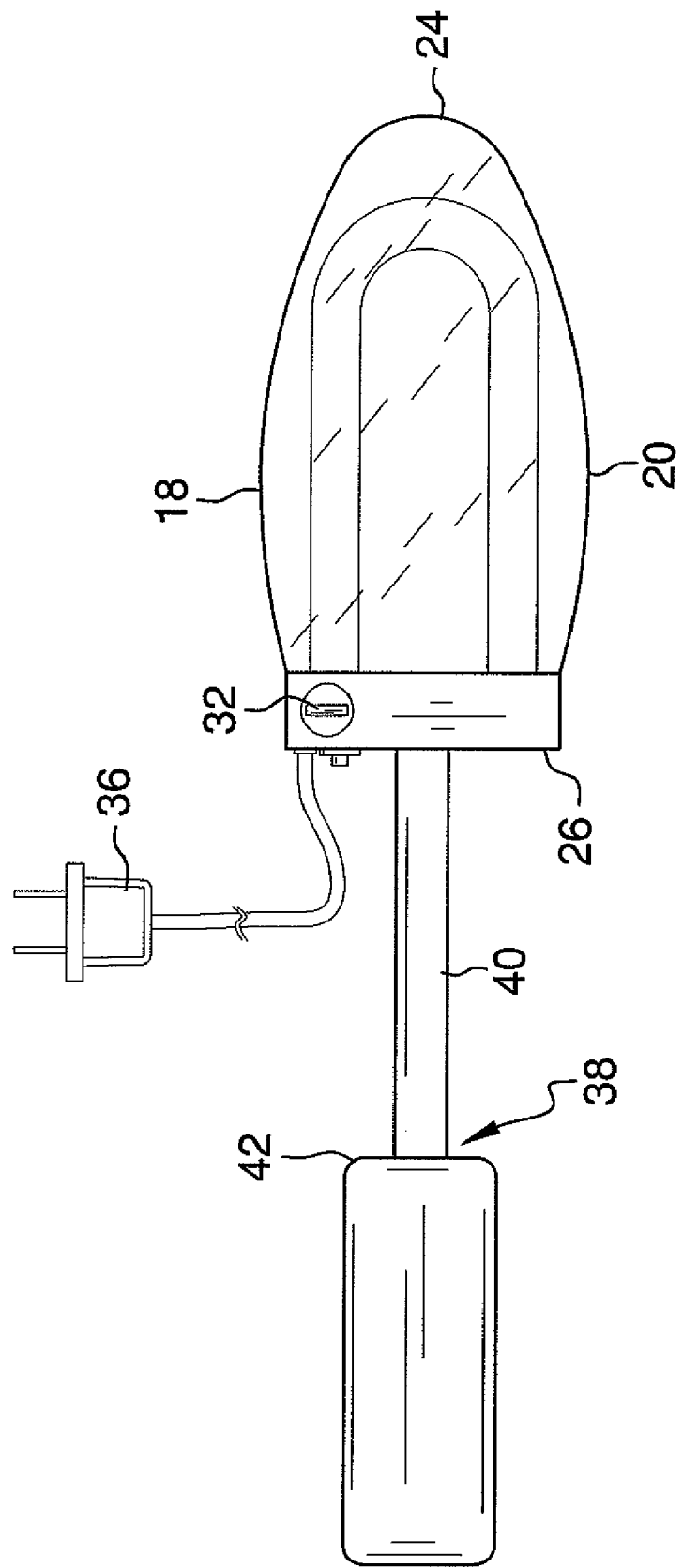
FIG. 4 is a top view of the present invention.
Figure 5:
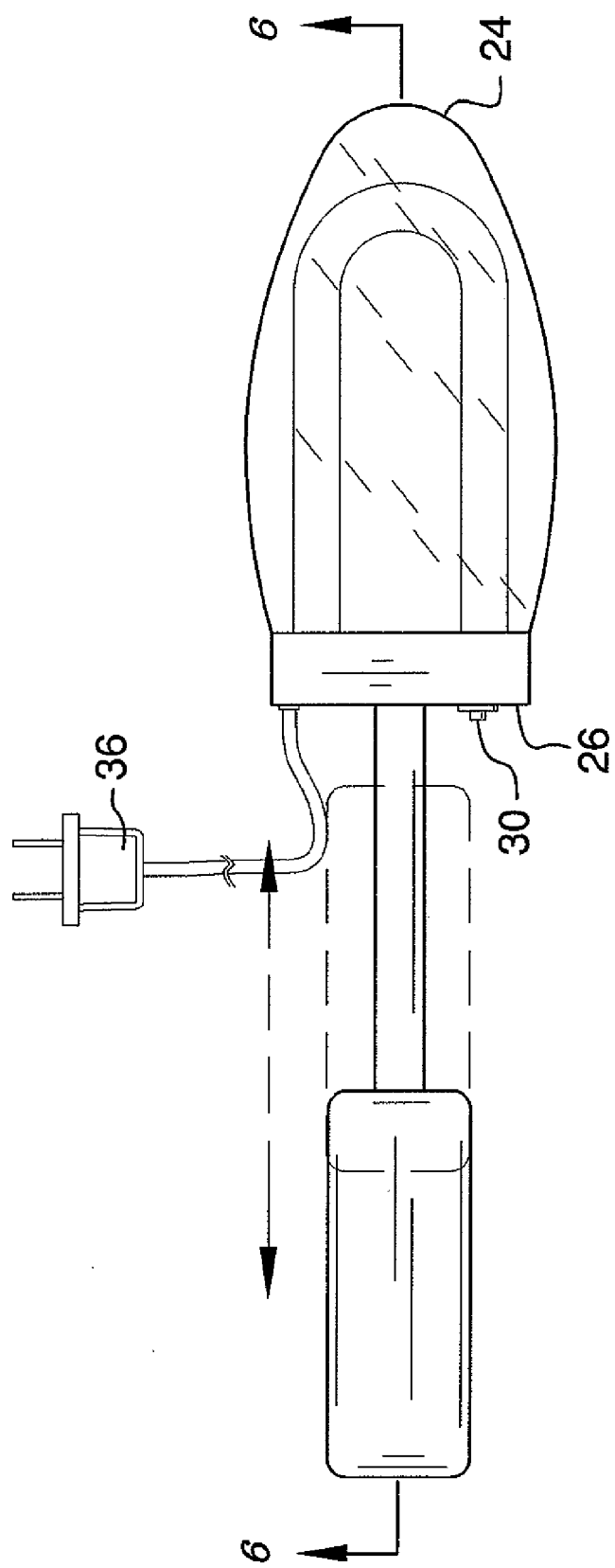
FIG. 5 is a bottom view of the present invention.
Figure 6:
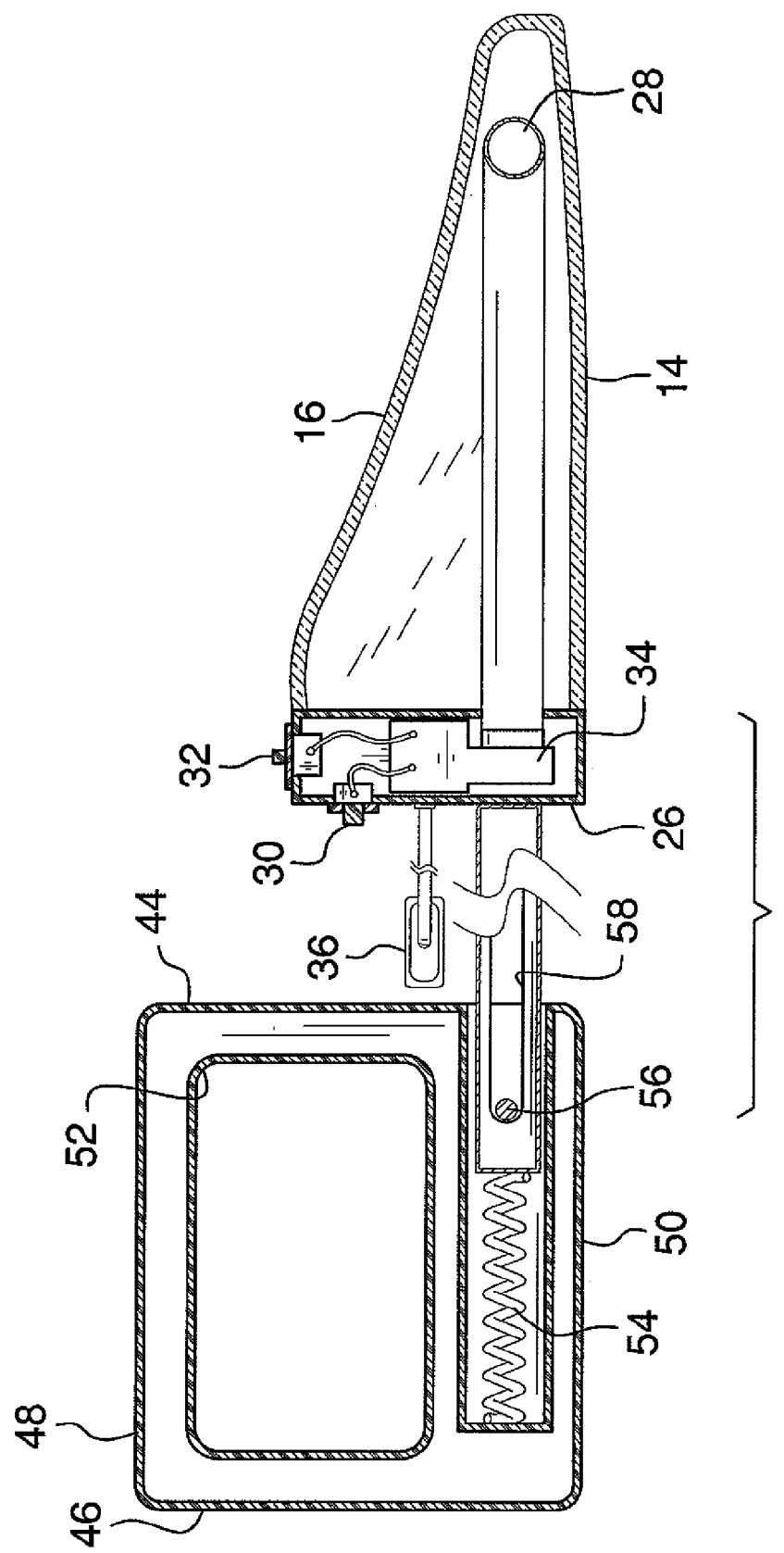
FIG. 6 is a cross-sectional view taken along line 6-6 of FIG. 5 of the present invention.
Figure 7:
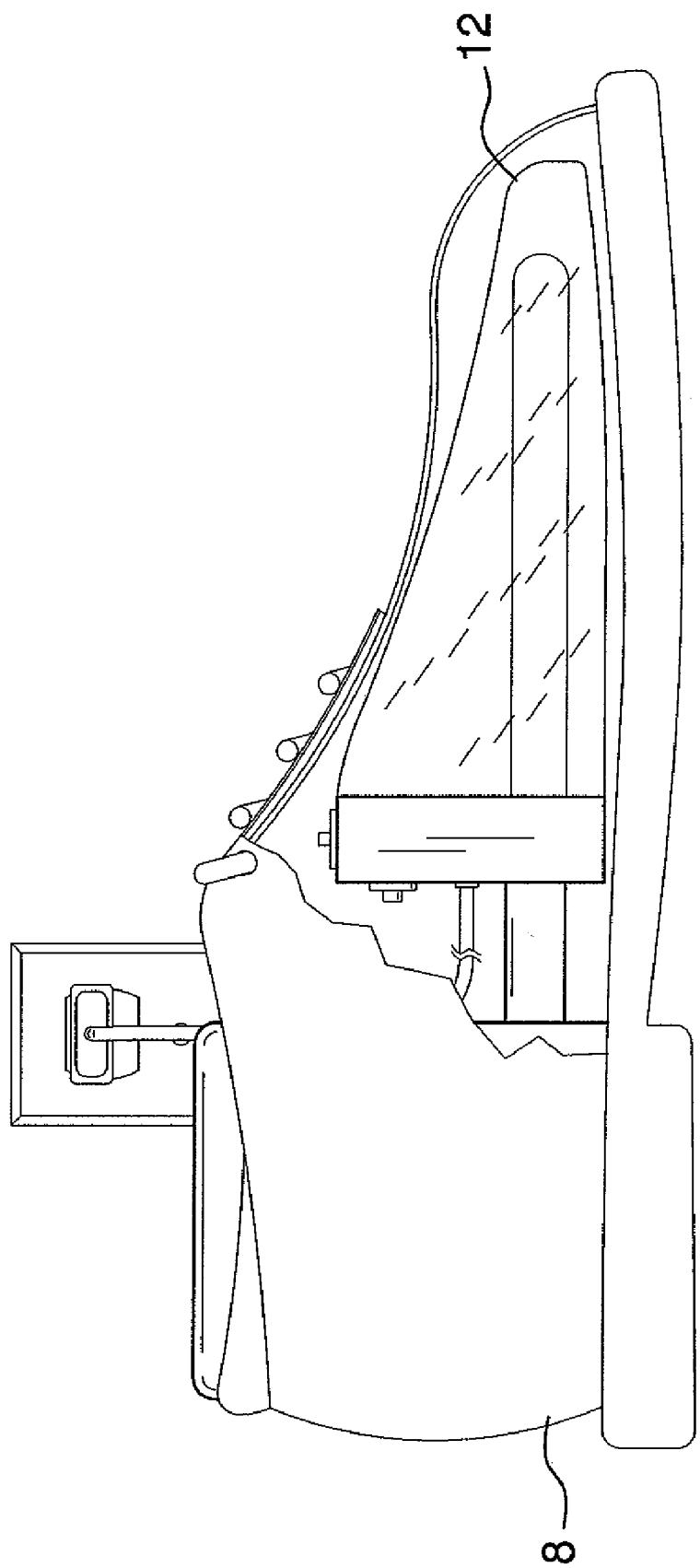
FIG. 7 is a die in-use view of the present invention.

With reference now to the drawings, and in particular to FIGS. 1 through 7 thereof, a new shoe sanitizing device embodying the principles and concepts of the present invention and generally designated by the reference numeral 10 will be described.

As best illustrated in FIGS. 1 through 7, the shoe sanitizing apparatus 10 generally comprises a housing 12 that has a bottom wall 14, a top wall 16, a first lateral wall 18, a second lateral wall 20, a front wall 24 and a rear wall 26. The top 16, bottom 14, first lateral 18, second lateral 20 and front 24 walls comprise a transparent material. The top wall 16 arcs downwardly from the rear wall 26 to the front wall 24. Each of the first 18 and second 20 lateral walls is convexly arcuate from the rear wall 26 to the front wall 24. The front wall 24 has a smaller width than the rear wall 26. This shape will allow the housing 12 to contour to the inner walls of a shoe 8 so that the housing 12 pushes out the creases and exposes a front portion of the shoe's 8 entire inner surface to light emitted by a light emitter 28 positioned within the housing 12. The light emitter 28 emits light that has a frequency to kill bacteria. In particular, this may be ultraviolet light.

An actuator 30 is operationally coupled to the light emitter 28. The light emitter 28 is turned on or off when the actuator 30 is actuated. The actuator 30 is positioned on the rear wall 26. A timer 32 is operationally coupled to the light emitter 28. The timer 32 is actuated to selectively determine a length of time that the light emitter 28 is turned on. The timer 32 is positioned on the rear wall 26. The light emitter 28 may be powered by a battery 34, mounted in the rear wall 26, which may be rechargeable. Alternatively, or in addition to the battery 34, a power cord 36 may be used with is electrically coupled to the light emitter 28 and which may be plugged into an electrical outlet.

A brace 38 is attached to the rear wall 26. The brace 38 releasably braces the housing 12 within a front portion of the shoe 8. The brace 38 includes a rod 40 that is attached to and extends rearward of the rear wall 26. A block 42 has a forward side 44, a rearward side 46, an upper side 48 and a lower side 50. The rod 40 extends into the forward side 44 and is extendable into and outwardly of the forward side 44. The block 42 has an aperture 52 extending therethrough which defines a grip. A biasing member 54 is positioned within the block 42 and biases the rod 40 outwardly of the block 42. The biasing member 54 comprises a spring. A locking pin 56 is positioned in the block 42 and extends through and elongated slot 58 in the rod 40 to prevent the rod from being pulled completely from the block 42.

In use, the housing 12 is positioned within the shoe 8 and the light emitter 28 turned on to kill bacteria in the shoe 8. The time the light emitter 28 emits light may be adjusted so that a user of the apparatus 10 need not return to the shoe 8 to turn the light emitter 28 off. By killing the bacteria, odors will be reduced and prevented.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A shoe sanitizing apparatus comprising:
   a housing having a bottom wall, a top wall, a first lateral wall, a second lateral wall, a front wall and a rear wall, said top, bottom, first lateral, second lateral and front walls comprising a transparent material;
   a light emitter being positioned within said housing, said light emitter emitting light having a frequency to kill bacteria;
   an actuator being operationally coupled to said light emitter, said light emitter being turned on or off when said actuator is actuated;

a brace being attached to said rear wall, said brace releasably bracing said housing within a front portion of a shoe, said brace including;
   a rod being attached to and extending rearward of said rear wall;
   a block having a forward side, a rearward side, an upper side and a lower side, said rod having a pair of lateral sides, each of said upper, lower, forward and rearward sides extending between said lateral sides, said block extending into said forward side and being extendable into and outwardly of said forward side, said block having an aperture extending therethrough defining a grip, said aperture extending through said lateral sides and being spaced between and spaced from said upper and lower sides; and
wherein said housing is positioned within a shoe and said light emitter turned on to kill bacteria in the shoe.

2. The apparatus according to claim 1, wherein said top wall arcs downwardly from said rear wall to said front wall, each of said first and second lateral walls being convexly arcuate from said rear wall to said front wall, said front wall having a smaller width than said rear wall.

3. The apparatus according to claim 1, wherein said light emitter emits ultraviolet light.

4. The apparatus according to claim 1, further including a timer being operationally coupled to said light emitter, said timer being actuated to selectively determine a length of time that said light emitter is turned on.

5. The apparatus according to claim 1, further including a biasing member being positioned within said block, said biasing member biasing said rod outwardly of said block.

6. A shoe sanitizing apparatus comprising:
   a housing having a bottom wall, a top wall, a first lateral wall, a second lateral wall, a front wall and a rear wall, said top, bottom, first lateral, second lateral and front walls comprising a transparent material, said top wall arcing downwardly from said rear wall to said front wall, each of said first and second lateral walls being convexly arcuate from said rear wall to said front wall, said front wall having a smaller width than said rear wall;
   a light emitter being positioned within said housing, said light emitter emitting light having a frequency to kill bacteria, said light emitter emitting ultraviolet light;
   an actuator being operationally coupled to said light emitter, said light emitter being turned on or off when said actuator is actuated, said actuator being positioned on said rear wall;
   a timer being operationally coupled to said light emitter, said timer being actuated to selectively determine a length of time that said light emitter is turned on, said timer being positioned on said rear wall;
   a brace being attached to said rear wall, said brace releasably bracing said housing within a front portion of a shoe, said brace including;
      a rod being attached to and extending rearward of said rear wall;
      a block having a forward side, a rearward side, an upper side and a lower side, said block having a pair of lateral sides, said upper, lower, forward and rearward sides extending between said lateral sides, said rod extending into said forward side and being extendable into and outwardly of said forward side, said block having an aperture extending therethrough and defining a grip, said aperture extending through said lateral sides and being spaced between and spaced from said upper and lower sides;
      a biasing member being positioned within said block, said biasing member biasing said rod outwardly of said block; and
   wherein said housing is positioned within the shoe and said light emitter turned on to kill bacteria in the shoe.

* * * * *